United States Patent [19]

Reichelt et al.

[11] Patent Number: 5,347,032

[45] Date of Patent: Sep. 13, 1994

[54] PREPARATION OF ALKYL CYANOACETATES

[75] Inventors: Helmut Reichelt, Neustadt; Clemens Grund, Mannheim, both of Fed. Rep. of Germany

[73] Assignee: BASF Aktiengesellschaft, Ludwigshafen, Fed. Rep. of Germany

[21] Appl. No.: 100,360

[22] Filed: Aug. 2, 1993

[30] Foreign Application Priority Data

Aug. 20, 1992 [DE] Fed. Rep. of Germany ....... 4227505

[51] Int. Cl.$^5$ .................. C07C 253/14; C07C 253/30
[52] U.S. Cl. .................................................. 558/443
[58] Field of Search ........................................ 558/443

[56] References Cited

U.S. PATENT DOCUMENTS

| | | | |
|---|---|---|---|
| 2,480,380 | 8/1949 | Nicholl et al. | 558/443 |
| 2,553,065 | 5/1951 | Somogyi et al. | 558/443 |
| 3,668,231 | 6/1972 | Rosin et al. | 558/443 |
| 3,723,499 | 3/1973 | Barbezat et al. | 558/443 |
| 4,174,347 | 11/1979 | Austermuhle-Bertola | 558/443 |

FOREIGN PATENT DOCUMENTS

| | | |
|---|---|---|
| 1939080 | 2/1970 | Fed. Rep. of Germany . |
| WO92/12962 | 8/1992 | PCT Int'l Appl. . |
| 1231521 | 5/1971 | United Kingdom . |

OTHER PUBLICATIONS

Carbonsäuren und Carbonsäure-Derivate; Jürgen Falbe, et al; Gerog Thieme Verlag Stuttgart, New York; pp. 659–660; (1985).

Landolt-Börnstein Azhlenwerte und Fun Ktionen Aus Physisk, Chemie, Astronimie, Geophysik und Technik; Berlin-Göttingen-Heidelberg; Springer-Verlag; (1960) pp. 663–664.

Chemical Abstracts; vol. 82, No. 23, Jun. 9, 1975; Alovitdinov, et al.; 82:155242x.

Primary Examiner—Joseph Paul Brust
Attorney, Agent, or Firm—Oblon, Spivak, McClelland, Maier & Neustadt

[57] ABSTRACT

A process for the preparation of $C_4$–$C_{10}$alkyl cyanoacetates by the reaction of cyanoacetic acid with $C_4$–$C_{10}$alkanols at a temperature of from 35° to 150° C. and under a pressure of from 70 to 1013 mbar, in the presence of catalytic amounts of acid, while a $C_4$–$C_{10}$alkanol/water azeotrope is separated during the reaction.

5 Claims, No Drawings

PREPARATION OF ALKYL CYANOACETATES

The present invention relates to a novel process for the preparation of $C_4$-$C_{10}$alkyl cyanoacetates by the reaction of cyanoacetic acid with $C_4$-$C_{10}$alkanols.

DE-A 1,938,080 discloses a method of extracting cyanoacetic acid from aqueous solution by means of n-butanol and converting the extract to n-butyl cyanoacetate in the presence of toluenesulfonic acid with removal of the water of reaction by azeotropic distillation. It has been found, however, that when this procedure is used the extraction of cyanoacetic acid from the aqueous phase is not carried to completion.

It is thus an object of the present invention to provide a novel process for the preparation of $C_4$-$C_{10}$alkyl cyanoacetates, in which an aqueous cyanoacetic acid solution is again used as starting point, but in which there is no need to extract the cyanoacetic acid.

We have now found that the preparation of a $C_4$-$C_{10}$alkyl cyanoacetate by the reaction of cyanoacetic acid with a $C_4$-$C_{10}$alkanol is achieved in an advantageous manner when cyanoacetic acid is caused to react, in an aqueous medium, with from 5 to 30 times its molar amount of a $C_4$-$C_{10}$alkanol at a temperature of from 35° to 150° C. and under a pressure of from 70 to 1013 mbar, in the presence of a catalytic amount of an acid, while a $C_4$-$C_{10}$alkanol/water azeotrope is separated off during the reaction.

$C_4$-$C_{10}$alkanols suitable for use in the process of the invention are, e.g., butanol, isobutanol, sec-butanol, tert-butanol, pentanol, isopentanol, neopentanol, tert-pentanol, and hexanol, 2-methylpentanol, heptanol, 2-methylhexanol, octanol, isooctanol, 2-ethylhexanol, nonanol, isononanol, 2-methyloctanol, decanol, isodecanol or 2-methylnonanol.

The above designations isooctanol, isononanol and isodecanol are trivial names and refer to the alcohols obtained in the oxo synthesis (cf *Ullmanns Encyklopadie der technischen Chemie,* 4th Edition, Vol. 7, pp. 215 to 217, and also Vol. 11, pp. 435 and 436.)

A technique for the preparation of $C_4$-$C_8$alkyl cyanoacetate is preferred, and the preparation of $C_4$ alkyl cyanoacetates is of special significance.

In the process of the invention, the esterification of cyanoacetic acid is carried out in an aqueous medium. The starting point is usually an aqueous cyanoacetic acid solution which has a content of cyanoacetic acid of from 20 to 70 wt. % and preferably from 60 to 70 wt. %, based, in each case, on the weight of the solution.

For each mole of cyanoacetic acid there are usually used from 5 to 30 mol, and preferably from 15 to 20 mol, of $C_4$-$C_{10}$alkanol.

According to the invention, the esterification is carried out in the presence of a catalytic amount of an acid. Suitable acids are, in particular, strong to moderately strong inorganic or organic acids, such as sulfuric acid, hydrochloric acid, phosphoric acid, benzenesulfonic acid, o- or p-toluenesulfonic acid, methane-sulfonic acid, trifluoromethanesulfonic acid, trifluoroacetic acid, or mono-, di- or tri-chloroacetic acid. The use of sulfuric acid or p-toluenesulfonic acid is preferred, while the use of sulfuric acid is of greater significance.

Amounts of from 0.001 to 0.01 mol of acid are generally taken to be "catalytic amounts", based on 1 mol of cyanoacetic acid.

The process of the invention is carried out at a temperature of from 35° to 150° C. and preferably from 50° to 90° C.

The pressure used in the process of the invention is from 70 to 1013 mbar and preferably from 70 to 270 mbar.

Our novel process is conveniently carried out by placing aqueous cyanoacetic acid solution, $C_4$-$C_{10}$alkanol, and acid (catalyst) in suitable equipment at room temperature in the aforementioned ratio, heating the mixture to a temperature as specified in the present invention, setting the pressure to a value as specified in the invention, and at the same time commencing the separation of the $C_4$-$C_{10}$alkanol/water azeotrope.

We prefer to use a procedure in which the the reaction temperature is raised in steps.

In a particularly preferred embodiment of the process of the invention, the reaction mixture is first heated for from 1 to 2 h so as to raise the temperature to from 35° to 50° C. while the azeotropic mixture is distilled off completely under a pressure of from 70 to 270 mbar. Thereafter the reaction mixture is heated for from 2 to 5 h so as to raise the temperature to from 50° to 70° C. whilst keeping the pressure at the above value and with complete separation of the azeotropic mixture. Then finally the reaction mixture is heated for from 2 to 5 h so as to raise the temperature to from 70° to 120° C. whilst keeping the pressure at the above value and allowing the azeotropic mixture to distill off, this temperature being maintained for a further 5 to 20 h. In this last phase of the reaction it is particularly advantageous to distill off the azeotropic mixture at a ratio of withdrawn to recycled material of from 9:99 to 4:80.

On completion of the reaction, which generally takes from 15 to 25 h, the reaction mixture is cooled and the equipment ventilated. The distillation residue is then filtered and excess $C_4$-$C_{10}$alkanol is distilled off from the filtrate.

The $C_4$-$C_{10}$alkanol produced during the azeotropic distillation or during the "post-distillation", can be recycled to the process.

The $C_4$-$C_{10}$alkyl cyanoacetates concerned are valuable intermediates for the preparation of active substances, adhesives or coloring agents. Depending on the intended usage of the product the distillation residues containing the target product can be used directly for further synthesis steps or are alternatively subjected to superfractionation.

By means of our novel process, which can be carried out batchwise or continuously, $C_4$-$C_{10}$alkyl cyanoacetates can be prepared in a simple manner, accomplishing a good space-time yield and a high degree of purity. One special advantage of our novel process is that it can be carried out in aqueous medium, i.e., for example, an aqueous solution of cyanoacetic acid can be used directly as produced in the synthesis of cyanoacetic acid.

The invention is illustrated below with reference to the following examples.

EXAMPLE 1

475 g of 70 wt % strength aqueous cyanoacetic acid, 1215 g of n-butanol and 10.25 g of concentrated sulfuric acid were placed in a reaction vessel. Heat was applied for 1 h to raise the inside temperature to 42° C. and the pressure was adjusted to 70 mbar, and at 36° C. and above the n-butanol/water azeotrope began to distill off and was fully withdrawn. Heat was then applied over a period of 3 h to raise the temperature to 62° C. and the azeotropic mixture was fully withdrawn over a transition temperature range of from 36° to 53° C. Heating of the reaction mixture was then continued for one hour (bath temperature: 112° C.) and kept at this temperature for a period of 8 h, while the optimum azeotropic mixture distilled off at a ratio of withdrawn to recycled material of 5:80 over a transition temperature range of from 46° to 57° C., and the inside temperature finally rose to 90° C. (boiling point of n-butanol at 70 mbar). The batch was cooled over 3 h to 20° C. and the equipment was ventilated.

The distillation residues were filtered and the filtrate freed from residual n-butanol by means of distillation. 572.7 g of crude product were obtained which exhibited a content von 93% (GC) of n-butyl cyanoacetate.

EXAMPLE 2

Example 1 was repeated except that the crude product was distilled under a pressure of 1 mbar (boiling point: 79°–81° C.). The n-butyl cyanoacetate was obtained at a purity exceeding 98% (GC).

EXAMPLE 3

495.2 g of 68.7 wt % strength aqueous cyanoacetic acid, 1215 g of n-butanol and 5 g of p-toluenesulfonic acid were placed in a reaction vessel. Heat was applied for 3 h to raise the inside temperature to 60° C., and the pressure was adjusted to from 72 to 69 mbar. While effecting full withdrawal the n-butanol/water azeotrope distilled overhead at 38° C. and higher. The pressure was then adjusted to 150 mbar and the batch heated to from 70° to 80° C., and the azeotropic mixture was withdrawn at a ratio of withdrawal to recycled material of 9:99 over a period of 16 h (transition temperature: 53° to 60° C.). The batch was cooled to room temperature over a period of 3 h and the equipment was ventilated. Distillation residues were filtered and the filtrate freed from residual n-butanol. The resulting crude product had a content of n-butyl cyanoacetate of 90% (GC).

EXAMPLE 4

495.2 g of 68.7 wt % strength aqueous cyanoacetic acid, 1500 mL of isobutanol and 5 g of p-toluenesulfonic acid were heated to 80° C. in 3 h under a pressure of ca 270 mbar, and the water/isobutanol azeotrope was removed completely. Stirring was then continued for a further 14 h at a ratio of withdrawn to recycled material of 11:99, to give a transition temperature of 67° C. and a final temperature of 88° C. at 200 mbar. Excess isobutanol was distilled off after filtration and 529 g of crude isobutyl cyanoacetate (purity as measured by GC analysis: 90%) were obtained.

We claim:

1. A process for the preparation of a $C_4$–$C_{10}$alkyl cyanoacetate by the reaction of cyanoacetic acid with a $C_4$–$C_{10}$alkanol, comprising reacting cyanoacetic acid in an aqueous medium, with from 5 to 30 times its molar amount of a $C_4$–$C_{10}$alkanol at a temperature of from 35° to 150° and under a pressure of from 70 to 1013 mbar, in the presence of a catalytic amount of an acid, while a $C_4$–$C_{10}$ alkanol/water azeotrope is separated during the reaction, and wherein said cyanoacetic acid is not extracted from said aqueous medium prior to esterification.

2. A process as claimed in claim 1, wherein cyanoacetic acid is caused to react with a $C_4$–$C_8$alkanol.

3. A process as claimed in claim 1, wherein the reaction is carried out at a temperature of from 50° to 90° C.

4. A process as claimed in claim 1, wherein the reaction is carried out under a pressure of from 70 to 270 mbar.

5. A process as claimed in claim 1, wherein the reaction is carried out using an aqueous cyanoacetic acid solution which contains from 20 to 70 wt % of cyanoacetic acid, based on the total weight of the solution.

* * * * *